United States Patent [19]

Haber

[11] Patent Number: 4,551,862
[45] Date of Patent: Nov. 12, 1985

[54] PROSTHETIC SPHINCTER

[76] Inventor: Terry M. Haber, 25011 Castlewood, Lake Forest, Calif. 92630

[21] Appl. No.: 435,761

[22] Filed: Dec. 15, 1982

[51] Int. Cl.$^4$ ............................................. A61F 1/00
[52] U.S. Cl. .................................... 623/14; 128/1 R; 128/DIG. 25; 128/678; 128/676
[58] Field of Search ....... 128/1 R, 678, 676, DIG. 25; 354/226, 270, 269; 3/1, 1.4, 1.5

[56] References Cited

U.S. PATENT DOCUMENTS

| | | | |
|---|---|---|---|
| 1,170,208 | 2/1916 | Wollensak | 354/269 |
| 1,741,526 | 12/1929 | Kohl | 354/269 |
| 2,217,718 | 11/1940 | Ulano | 354/270 |
| 2,269,401 | 1/1942 | Steiner | 354/270 |
| 3,675,657 | 7/1972 | Gauthier | 128/327 |
| 4,118,805 | 11/1978 | Reimels | 128/DIG. 25 |
| 4,256,094 | 3/1981 | Kapp et al. | 128/DIG. 25 |
| 4,399,809 | 8/1983 | Baro et al. | 128/DIG. 25 |
| 4,401,107 | 8/1983 | Haber et al. | 3/1 |

FOREIGN PATENT DOCUMENTS 1174814 12/1969 United Kingdom ....... 128/DIG. 25

Primary Examiner—Richard J. Apley
Assistant Examiner—David J. Isabella
Attorney, Agent, or Firm—Morland C. Fischer

[57] ABSTRACT

A prosthetic sphincter is designed to surround a waste elimination passage in a patient, such as the lower colon or urethra for realizing continence. The artificial sphincter itself comprises a stationary ring and a rotatable ring supported for rotation by the stationary ring. Three occlusion elements extend from 120° circumferentially spaced points on the rotatable ring to similarly oriented points on the stationary ring, offset from the first dimensioned points by a given number of degrees. The length of the various elements is such that when the rotatable ring is in a first position, the elements follow the inner peripheral curvature of the rings to maximize the opening through the rings and thus through the elimination passage circumscribed by said rings. When the rotatable ring is rotated to a second position, the displacement of the second ends of the elements from the first ends is increased, to cause all three elements to enter the opening and thereby occlude the elimination passage contained therein by applying pressure at 120° circumferentially spaced areas, or at the appropriate angular degree division(s) with respect to the selected number of occlusion elements to achieve a state of prosthetic continence.

17 Claims, 8 Drawing Figures

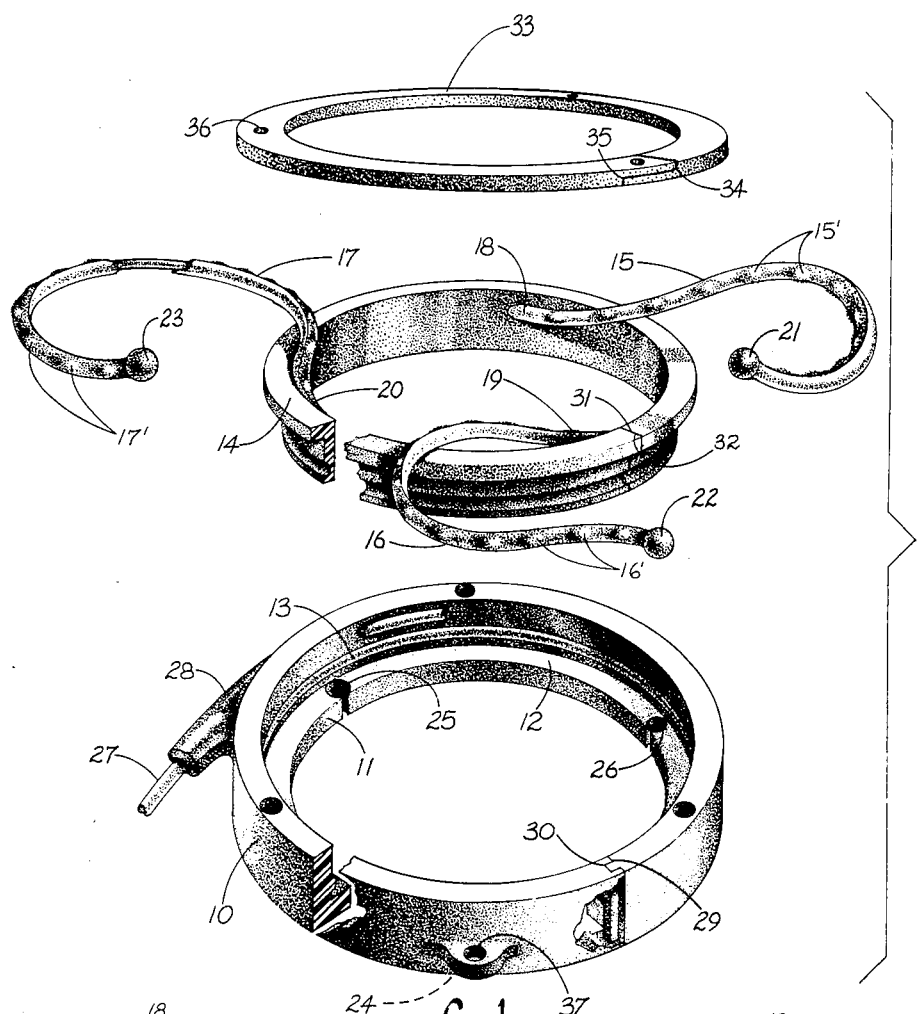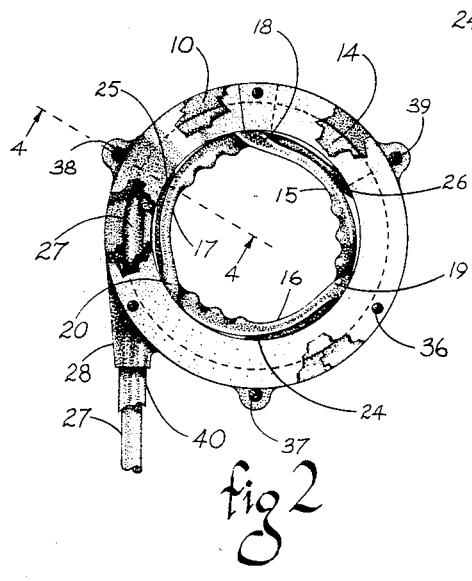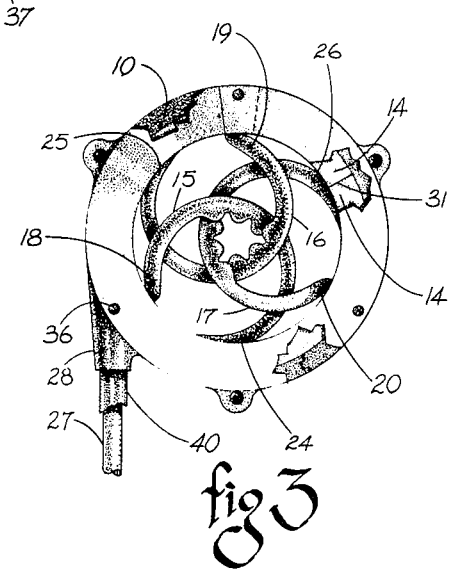

PROSTHETIC SPHINCTER

FIELD OF THE INVENTION

The present invention relates to prosthetic sphincters for implantation in a patient to overcome the problem of incontinence.

BACKGROUND OF THE INVENTION

Conventional colostomies involve a surgical procedure in which the intestine is severed and an end of the intestine is exteriorized through an incision in the abdominal wall of a patient. The anastomosis of the intestine to the peritoneum and skin of the abdominal wall is such as to provide a passage for intestinally-contained fecal matter to pass to the outside of the patient's body. The nipple-like termination of this passage is called the "stoma", the Latin term for "mouth".

The foregoing operation results in a loss of continence for the patient and he or she must typically wear a polymer pouch on the outside of the body or a reconstructed pouch of surgically enlarged intestinal tissue on the inside of the body in order to collect the fecal matter passing through the abdominal stoma, which additionally necessitates surgical relocation of the intestine from its natural anal opening to an artificial abdominal stoma site. In order to avoid such incontinence several types of occlusion devices have been proposed for closing off the stoma in order that a patient need not be burdened with a pouch. No such device has had either a true, sphincter-like, mechanical action or allowed the intestinal transcutaneous elimination passage to remain in its natural location.

Most such closure devices require a complicated surgical procedure, involving an invasion into the intestine itself. Furthere, any such closure device located on the abdominal wall or immediately beneath the abdominal wall of the area of the stoma is "unnatural" in its specific location.

Aside from proper control of the lower colon by appropriate closure devices, there is further a need for the use of such devices in controlling other eliminating passages such as the urethra for post prostatectomy patients, having undergone the trans-urethral resection procedure.

BRIEF DESCRIPTION OF THE PRESENT INVENTION

With the foregoing in mind, the present invention contemplates the provision of a greatly improved closure device in the form of a synthetic sphincter which can be readily surgically implanted without invading the particular elimination passage such as the intestine itself and furthermore which can be located at the anal-positioned end of the intestine when used in the fecal elimination passage in, or proximal to, the normal or "natural" position of the sphincter muscle. Further, the design of this prosthetic sphincter is such that it will close off the descending intestine or lower colon of a patient in a manner analogous to the operation of the normal sphincter muscle so that maximum comfort to the patient is realizable. Further, the device can be miniaturized for use in precisely controlling occlusion of even the smaller diameter pediatric urethra in a manner similar to the occlusion action upon the lower colon.

Briefly, the prosthetic sphincter includes a stationary ring and a rotatable ring axially aligned with the stationary ring to define a ring assembly with an opening through the rings. An occlusion spring means interconnects the stationary ring and the rotatable ring such that rotation of the rotatable ring relative to the stationary ring from a first to a second position causes the occlusion spring means to enter the orifice opening to occlude any elimination passage about which the ring assembly has been positioned and to maintain the passage in an occluded position until the rotatable ring is rotated back to its first position relative to the stationary ring.

BRIEF DESCRIPTION OF THE DRAWINGS

A better understanding of this invention will be had by now referring to the accompanying drawings in which:

FIG. 1 is an exploded perspective view of basic components making up the prosthetic sphincter of this invention;

FIG. 2 is a top plan view partly broken away of the components of FIG. 1 in an assembled relationship showing the assembly in open condition;

FIG. 3 is a view similar of FIG. 2 but illustrating the position of certain components when the assembly is in closed position;

DETAILED DESCRIPTION OF THE INVENTION

Figure 4:
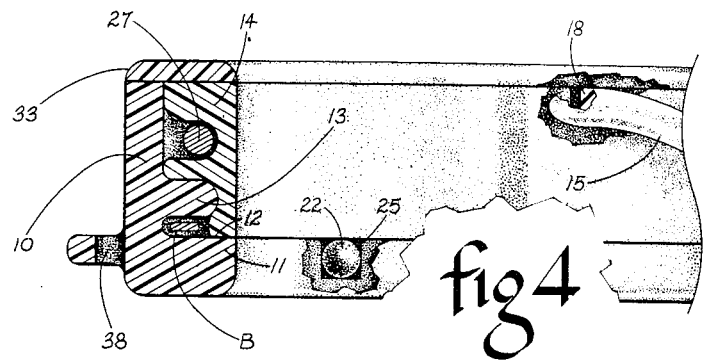
FIG. 4 is a greatly enlarged fragmentary cross section taken in the direction of the arrows 4—4 of FIG. 2.

Referring first to the lower portion of FIG. 1, the prosthetic sphincter includes a stationary ring 10 having a radially inwardly directed flange 11 defining a flat ledge 12 facing generally upwardly. A spacer bead 13 extends circumferentially around the inside periphery of the stationary ring 10.

Shown exploded above the stationary ring 10 is a rotatable ring 14 arranged to be rotatably mounted and supported by the stationary ring 10 in coaxial relationship therewith. In this respect, the flat ledge 12 will seat the bottom of the rotatable ring 14 while the spacer bead 13 surrounds the outer periphery of the ring 14 and holds it in a concentric position relative to the stationary ring, as well as serving a snapping assembly and holding function.

Referring more in detail to the ring 14, there are provided occlusion spring element means in the form of individual elongated bendable elements 15, 16 and 17, secured at first ends to the rotatable ring at 120° circumferentially spaced points as indicated at 18, 19 and 20 respectively. Second ends of these elements terminate in small spheres 21, 22 and 23 respectively receivable in securement cavities 24, 25 and 26 in the stationary ring 10. It will be evident that when respectively received in these cavities, the second ends of the elements are secured to the stationary ring at 120° circumferentially spaced points, in turn, respectively circumferentially displaced from the first mentioned circumferentially spaced points for the first ends a given number of degrees. As will become evident as the description proceeds, the given length of the elements and the given number of degrees is such that when the rotatable ring is in a first position, the elements follow the inner periphery of the rings to maximize the opening through the rings and when the rotatable ring is in a second position, the displacement of the second ends from the first ends is increased to cause all three elements to enter the opening through the rings to thereby adjustably occlude such opening.

The foregoing referred-to rotation of the rotatable ring 14 relative to the stationary ring 10 is accomplished by a force-applying means in the form of a cable 27 passing from a housing 28 on the stationary ring 10 at one end and having its other end arranged to be wound about the rotatable ring 14 when the ring 14 is nested within the ring 10.

In order that the stationary and rotatable ring can be positioned about an elimination passage in a patient's body such as the lower colon, the rings are split so that opposed ends can be separated. Thus, with respect to the stationary ring 10 and as illustrated in FIG. 1, opposed ends 29 and 30 define a separable portion on the circumference of the ring, the ring itself being made of a resilient biocompatible polymer material. Similarly there is provided a split defined between opposing ends 31 and 32 for the rotatable ring 14.

A cap or cover 33 shown in the top portion of FIG. 1 is provided to hold the ring assembly together and this cap 33 has opposed ends 34 and 35 overlapping as indicated to define a split which can be separated.

Because the second ends of the bendable elements or occlusion means 15, 16 and 17 are detachable from the receiving cavities 24, 25 and 26 in the stationary ring 10, and by virtue of the split ring constructions and split cover, the various components can be assembled about the lower intestine or colon without having to feed the intestine or colon through the opening. Once the rings and cover have been properly positioned to surround the lower colon, the second ends in the form of the small spheres of the occlusion means 15, 16 and 17 are received in the receiving cavities 24, 25 and 26 of the stationary ring 10 and thereafter the cover or cap 33 is then positioned over the rotatable ring 14 after the same has been properly nested in the stationary ring 10. Appropriate fastening holes such as indicated at 36 on the cap or cover 33 are provided to secure the assembly.

To assure proper anchoring of the ring assembly in a desired position within the patient's body, appropriate suture eyelets such as indicated at 37 in FIG. 1 and at 120° spaced circumferential points indicated at 38 and 39 in the plan view of FIG. 2 are provided. These eyelets may be integrally formed with the stationary ring 10 as shown, or attached using mesh-reinforced, silicone polymer, suture-anchoring appendages.

With specific reference to both FIGS. 2 and 3, the first ends of the bendable elements 15, 16 and 17 are again indicated by the numerals 18, 19 and 20 respectively. The second ends of these elements connecting to the stationary ring are respectively in positions indicated at 24, 25 and 26, the same being circumferentially displaced at least 180°. The lengths of the elements and the displacement between the first and second ends is such that when the rotatable ring is in a first position as depicted in FIG. 2, the elements follow the inner periphery of the rings to maximize the opening through the rings as described and as shown in FIG. 2. When the rotatable ring is rotated to a second position to increase the displacement of the second ends from the first ends, such action will cause the elements 15, 16 and 17 to enter the opening through the rings as depicted in FIG. 3 and thereby occlude the passage through the rings. The rotation from the first position to the second position of the rotatable ring as depicted, respectively, in FIGS. 2 and 3 may be approximately, but by no means whatsoever limited to 110°. For example if the first end connection 18 for the closure element 15 is taken as a reference shown in the top portion of FIG. 2, it will be noted in FIG. 3 that after the rotatable ring has been rotated this point 18 will be displaced approximately 110° from its initial position in a counterclockwise direction.

It will be noted in the embodiment of FIGS. 1, 2 and 3 that the individual closure elements 15, 16 and 17 are provided with periodic enlargements indicated in FIG. 1 at 15', 16' and 17'. These periodic enlargements serve simultaneously as cushioning enlargements, and nonconstrictive arterial blood circulation occlusion relief passages to gently engage the elimination passage about which the ring assembly is positioned and effect occlusion of such passage, without interference with mesenteric arterial blood circulation thereto.

In addition to the above, the actuating cable 27 preferably moves within a cable sheath or housing 40 which is stationary. The manner in which the cable 27 is actuated will become evident as the description proceeds.

Further details of the ring assembly described in FIGS. 1 to 3 will be evident by now referring to the enlarged cross section of FIG. 4 wherein the rotatable ring 14 is shown in assembled relationship with the stationary ring 10. It will be noted that the bead 13 properly supports the rotatable ring 14 over 360° and "keys" the rotatable member 14 within the stationary ring 10. In this respect, the lower peripheral end of the rotatable ring 14 slightly increases in diameter but is so dimensioned that it can "snap" over the bead 13 into the position illustrated in FIG. 4. Beneath the bead 13 there may optionally be positioned an annular bead of antibacterial material designated B.

FIG. 4 also shows the force applying means in the form of the actuating cable 27 surrounding an outer peripheral portion of the rotatable ring 14. Further, the terminal end sphere 22 for the element 16 is shown received in the receiving cavity 25.

Figure 5:
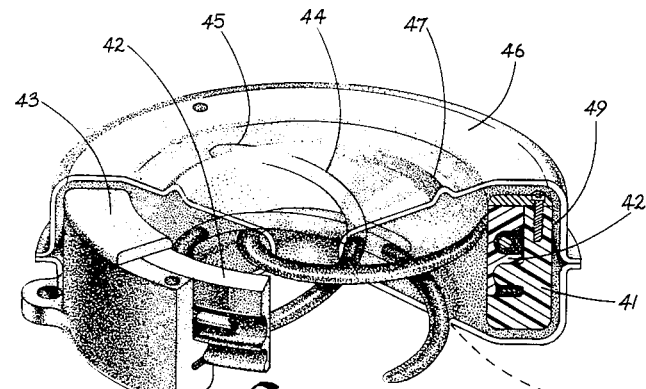
FIG. 5 is a broken away perspective view of a modified embodiment of the invention.

Referring now to FIG. 5, there is shown a modified form of the invention, wherein there is again provided a stationary ring 41 and a rotatable ring 42 held in position by means of a cover 43. Appropriate occlusion spring means or elements similar to those described are indicated by way of example at 44 having its first end secured at 45 to the rotatable ring. A tear resistant impervious skin or toroidal shape 46 surrounds the ring assembly and occlusion spring means. This skin 46 includes a plurality of annular elongation fatigue relief fold(s) shown at 47 and 48 on the top and bottom surfaces coaxial with the opening of the toroidal shape for accommodating the restriction of the opening through the ring assembly when the rotatable ring is moved to its second position. A gel-like pliable silicone polymer 49 is encapsulated within the toroidal shaped skin 46.

Figure 6:
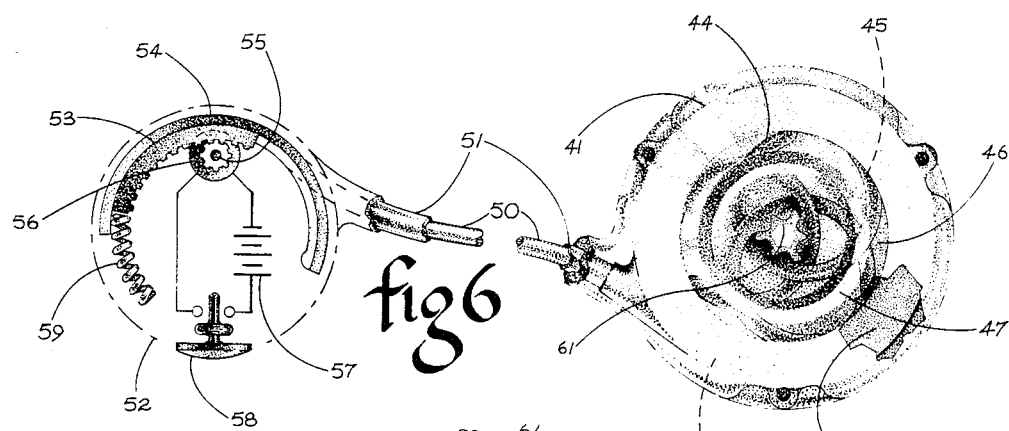
FIG. 6 is a bottom plan view partly schematic of the complete assembly of FIG. 5 with an appropriate control means.

FIG. 6 shows the ring assembly of FIG. 5 from the underside together with a cooperating force actuating means. In this respect, the cable for rotating the rotatable ring relative to the stationary ring is illustrated at 50, extending from a cable sheath 51. This cable 50 passes to a remote control housing depicted by the dashed circle 52 containing a rack 53 guided for movement within the housing by an appropriate guide 54. The cable 50 itself connects to one end of the rack 53. A pinion 55 driven by a motor 56 engages the rack 53 for moving the same when the motor is energized. Energization of the motor is accomplished by a battery 57 and appropriate operating switch button 58. A spring 59 within the housing 52 may be provided so that in the event of any failure, the rack 53 will be biased in a clockwise direction as viewed in FIG. 6 to urge the cable 50 out of the housing and thus restore the rotatable member to its first, non-occlusive position.

An important feature of this invention with respect to the foregoing is the fact that each of the bendable occlusion elements as described heretofore, may have a spring characteristic biasing it to a rectilinear position so that this spring characteristic tends to additionally assist to return the rotatable member to its first position in the absence of any force on the force applying cable. As a consequence, a fail safe system results. The spring 59 within the housing 52 is redundant in this respect but assures the fail safe feature.

Figure 7:
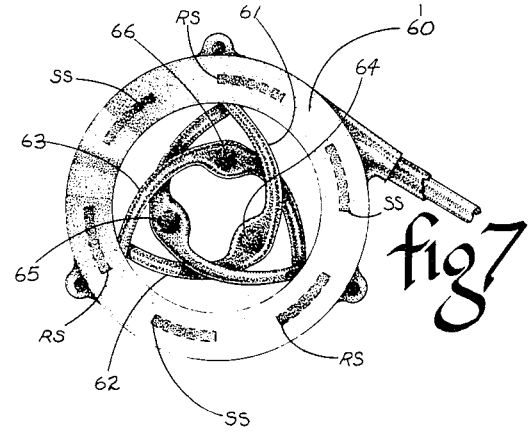
FIG. 7 is a top plan view of a further modified form of the invention.

FIG. 7 shows in plan view a further modified embodiment wherein a ring assembly 60 again includes three occlusion elements 61, 62 and 63 interconnecting the rotatable ring with a stationary ring. The stationary ring includes three sensor responsive means designated SS spaced at 120° on the ring. The rotatable ring in turn similarly includes three sensor responsive means also spaced at 120° as indicated at RS. When the rotatable ring is in the second position so that the elements have entered the opening to provide a restricted passage, then the sensor responsive means RS are displaced from the sensor responsive means SS and by utilizing an appropriate sensor exterior to the patient's body, the relative positions of the rings can thus be determined.

Another means for determining the degree of closure of the rings is to provide sensor responsive means directly in the bendable elements 61, 62, and 63. These sensor responsive means may be centrally positioned on the elements such as indicated at 64, 65 and 66 respectively, within the cushioning material. These latter sensor responsive means will again provide a means of determining the degree of closure of the elements from outside the patient's body. Examples of appropriate sensor responsive means are passive elements such as dense, X-ray opaque metals which will show up on a fluoroscope or X-ray machine or active elements such as minute rare earth magnets whose field can be readily detected.

Figure 8:
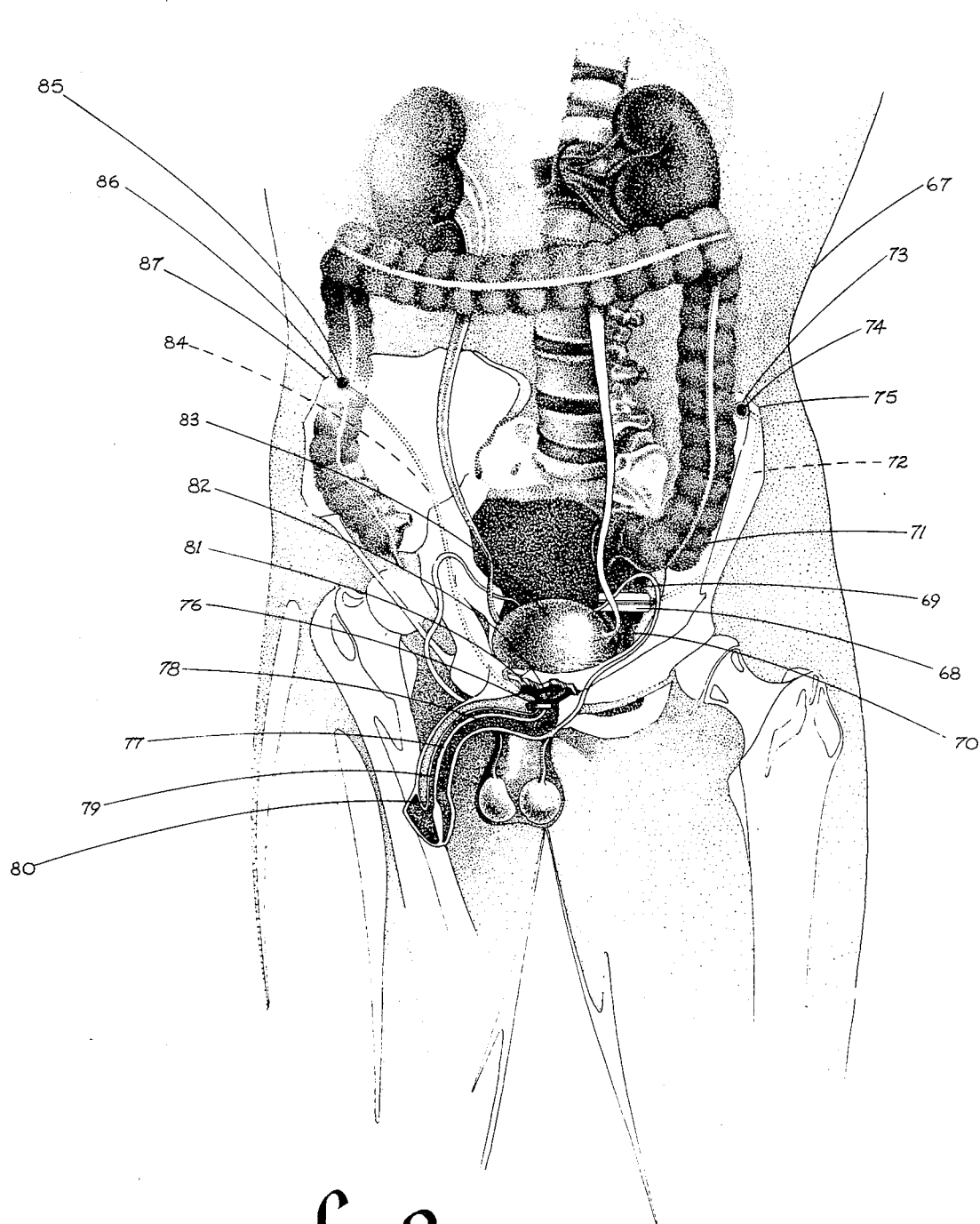
FIG. 8 is a fragmentary front view of a patient partly broken away illustrating the manner in which the prosthetic sphincter of this invention is used, to occlude the large intestine and/or the urethra.

Referring to FIG. 8, there are shown two examples of the manner in which the prosthetic sphincter of the present invention can be used. The first example is control of the lower intestine or colon and the second is control of the urethra.

Referring specifically to the right-hand portion of FIG. 8, there is shown a patient 67 wherein the prosthetic sphincter 68 is shown surrounding the lower colon or rectal elimination passage. The synthetic sphincter 68 itself is positioned between the superior rectal elimination passage 69 and the inferior rectal elimination passage or anal canal 70. These portions of the lower intestine are at the interface of the surgically reconstructed and/or relocated descending colon and the sigmoid colon 71.

The force applying means in the form of a control cable for the prosthetic sphincter 68 is indicated in dotted lines at 72 passing to an appropriate housing 73 incorporating a cable movement means such as described in FIG. 6. The operating push button is shown at 74, the housing and button being positioned in a surgically accessible subcutaneous area 75. It will be understood that the push button 74 can actually be operated by pressing at an appropriate place on the skin of the patient without having to invade the area. A momentarily applied pressure on the button will cause the prosthetic sphincter to be held in its closed position. A latch relay in the motor, for example, can be used.

Referring now to the left side portion of FIG. 8, there is shown a similar but smaller prosthetic sphincter 76 in accord with the present invention used to control the urethra. Towards this end, the prosthetic sphincter 76 is positioned about the upper portion of the urethral elimination passage 77 which extends within the corpus spongeosum shown at 78 and 79. The corpus spongeosum is adjacent to the corpus cavernosum 80. Above the prosthetic sphincter 76 is shown the urogenital diaphragm 81, prostate 82 and urinary bladder 83.

The actuating cable for the prosthetic sphincter 76 is indicated in dotted lines at 84 and extends to an appropriate housing 85 provided with a push button 86 and disposed in a surgically accessible subcutaneous area 87. In this instance, both of the surgically accessible areas 75 and 87 described in FIG. 8 are located at the ileal crests for purposes of increased ease of accessibility.

As described heretofore, the circumferential spacing of the connection points of the second ends of the occlusion elements from the first ends is at least 180° and may vary up to 270°. The additional displacement of the points connected to the stationary ring relative to the rotatable ring upon rotation of the rotatable ring between its first and second position may vary between appropriate values depending upon the initial displacement of the connecting ends to provide the desired degree of closure.

In referring to a "second" position assumed by the rotatable ring to effect occlusion of the elimination passage, it is to be understood that such second position is not fixed, but rather is a variable depending upon the state of the passage and other perameters. The "second" position is essentially that position which will effect an appropriate occulsion of the elimination passage with minimal mesenteric, arterial blood circulation interference or impedance.

Respecting the simple push button circuit shown in FIG. 6, it is to be understood, as noted heretofore, that a momentary pressing of the button 58 is all that is necessary to operate the motor 56, there being provided appropriate control circuitry which might include a latch relay responsive to simple electrical impulses to turn on and off. Any appropriate pressure control system can be provided to assure a constant closing pressure limited to a given value for safety purposes. Either electrical or wholly mechanical operating means can be provided in a modular arrangement if desired.

From all of the foregoing, it will now be appreciated that the present invention has provided an improved prosthetic sphincter which has a distinct advantage in that it can be assembled circumferentially about the colon or urethra without having to invade these elimination passages. Moreover, the overall axial length of the sphincter is kept relatively short by the nesting of the rotatable ring within the stationary ring and the provision of two or more closure elements as described. It is important that any prosthetic sphincter be kept of minimal mass and dimension and yet be capable of simulating the function of the natural sphincter.

Various changes and modifications falling within the scope and spirit of this invention will occur to those skilled in the art. The prosthestic sphincter, accordingly, is not be thought of as limited to the specific embodiments set forth merely for illustrative purposes.

I claim:

1. A prosthetic sphincter suitable for implantantion for embracing an elimination passage of a patient to control the movement of material therethrough for realizing continence, said sphincter including, in combination:
   (a) a stationary ring;
   (b) a rotatable ring axially aligned with said stationary ring to define a ring assembly having an occlusion opening through the rings for surrounding the patient's elimination passage;
   (c) occlusion spring means interconnecting said stationary ring and said rotatable ring such that rotation of said rotatable ring relative to said stationary ring from a first position causes said occlusion spring means to enter said occlusion opening to cause a closing of the occlusion opening around the elimination passage and a corresponding application of occlusive pressures to the elimination passage being surrounded by the rings to maintain the passage in an occluded condition until the rotatable ring is rotated back to its first position relative to the stationary ring; and
   (d) a tear resistant skin for enclosing said ring assembly and occlusion spring means, said skin having fatigue relief folds on top and bottom surfaces thereof arranged coaxially with the occlusion opening through said rings for accommodating the closing of the occlusion opening when the rotatable ring is moved from its first position, said skin having a pliable filling material located within the enclosure formed thereby for encapsulating said ring assembly and said occlusion spring means.

2. A prosthetic sphincter according to claim 1, in which said occlusion spring means comprises three individual elongated bendable and flexible elements, each having a spring characteristic biasing it to a rectilinear position and each having a given length essentially inextensible, said elements being secured at first ends to said rotatable ring at 120° circumferentially spaced points and at second ends to said stationary ring at 120° circumferentially spaced points, in turn, respectively circumferentially displaced from said first mentioned circumferentially spaced points a given number of degrees, said given length and said given number of degrees being such that when said rotatable ring is in said first position, the elements follow the inner periphery of the rings to maximize the opening through the rings and when said rotatable ring is in said second position, the displacement of the second ends from the first ends is increased to cause all three elements to enter the opening through the rings in an interwoven relationship to thereby restrict the passage when surrounded by the rings by applying pressure at 120° circumferentially spaced areas.

3. A prosthetic sphincter according to claim 1, including a force applying means connected to said rotatable ring and operable from a remote location to rotate said rotatable ring from its first position, the spring characteristic of said occlusion spring means being such as to return the rotatable ring to its first position in the absence of any force on said force applying means so that a fail safe system results.

4. A prosthetic sphincter according to claim 1, in which said stationary ring includes a radially inwardly directed flange on its inner periphery defining a ledge for seating and supporting said rotatable ring, both said stationary ring and rotatable ring having splits such that the opposed ring ends at the splits can be biased apart so that the rings can be positioned about said passage without requiring access to either end of the passage, the connection of said occlusion spring means to said stationary ring being separable to permit surrounding the passage by the ring assembly.

5. A prosthetic sphincter according to claim 2, in which said given number of degrees is from 180° to 270°.

6. A prosthetic sphincter according to claim 2, in which each of said elongated bendable elements includes periodic cushioning enlargements to gently engage the elimination passage and effect proper occlusion of the elimination passage.

7. A prosthetic sphincter according to claim 1, including sensor responsive means on each of said stationary ring and rotatable ring so that the relative rotational positions of the rings can be detected from outside the patient's body.

8. A prosthetic sphincter according to claim 2, in which each of said elongated bendable elements incorporates a sensor responsive means so that the degree of occlusion opening closure caused by the elements can be detected outside a patient's body.

9. A prosthetic sphincter according to claim 1, further including
   suture attachment means circumferentially spaced at outer peripheral portions of said stationary ring to enable attachment of the ring assembly to surrounding tissue, bone or facia; and
   anti-bacterial medium means disposed between said stationary and rotatable rings.

10. A prosthetic sphincter according to claim 3, in which said force applying means includes a cable extending around at least a peripheral portion of said rotatable ring and extending from said ring assembly to said remote location, said force applying means also including means for supplying an actuating force to said cable from said remote location to cause the rotation of said rotatable ring.

11. A prosthetic sphincter according to claim 10, in which
   said means for supplying an actuating force includes a motor, on-off switch means for controlling said motor, and rack and pinion means operated by said motor for supplying the actuating force to said cable, the remote end of said cable being connected to said rack and pinion means,
   said means for supplying an actuating force being implanted in a surgically accessible subcutaneous area of the patient's body proximal to an epidermal portion, such that said switch means can be manually operated at the epidermal portion.

12. An artificial sphincter comprising a prosthetic device suitable for implantation to embrace a patient's lumen for occluding and opening the lumen and controlling the movement of material therethrough, said sphincter comprising:

ring assembly means defining an occlusion orifice for surrounding the patient's lumen, said ring assembly means having a stationary ring and a rotatable ring axially aligned with and supported for rotation by said stationary ring;

a plurality of flexible occlusion elements extending between first circumferentially spaced locations at said rotatable ring and respective second circumferentially spaced locations at said stationary ring, such that when said rotatable ring is in a first position, said occlusion elements follow the inner periphery of said ring assembly means to maximize the size of the occlusion orifice as defined by said ring assembly means, and when said rotatable ring is rotated to a second position, said occlusion elements being extended and thereby caused to enter the occlusion orifice to overlap one another in an interwoven relationship and thereby cause both a closing of the occlusion orifice around the lumen and a corresponding application of occlusive pressures to the lumen being surrounded by said ring assembly means until said occlusion elements return to the first position, said occlusion elements having a spring-like characteristic for biasing said rotatable ring towards its first position; and force applying means interfaced with said rotatable ring to selectively rotate said rotatable ring to a particular second position whereby to adjustably vary the corresponding application of occlusive pressures to the patient's lumen;

said force applying means including cable means and switch means, said cable means surrounding and being rotatable around an outer peripheral portion of said rotatable ring for rotating said ring between the first and second positions, and said switch means being implanted at a location remote from said ring assembly means at a surgically accessible subcutaneous area of the patient's body proximal to an epidermal portion, such that said switch means can be manually operated at the epidermal portion to cause the rotation of said cable means and a corresponding rotation of said rotatable ring to the second position to thereby close said occlusion orifice and apply the occlusive pressures to the lumen being surrounded by said ring assembly means.

13. The artificial sphincter recited in claim 12, wherein said cable means extends from said ring assembly means to a remote location, at which remote location said switch means is operated to cause the rotation of said cable means and the corresponding rotation of said rotatable ring to the second position.

14. The artificial sphincter recited in claim 12, further comprising
a tear resistant envelope having a toroid shape for enclosing said ring assembly means and said occlusion elements, said envelope having annular fatigue relief folds on top and bottom surfaces thereof arranged coaxially with the occlusion orifice of said ring assembly means for accommodating the closing of the occlusion orifice when the rotatable ring is rotated from the first position, and
filler material located within said envelope and encapsulating said ring assembly means and occlusion elements.

15. The artificial sphincter recited in claim 12, further comprising sensor responsive means located on each of said rotatable and stationary rings, so that the positions of said rings relative to one another can be detected by a sensor from outside the patient's body.

16. The artificial sphincter recited in claim 12, further comprising sensor responsive means located on each of flexible occlusion elements, so that the positions of said occlusion elements relative to said occlusion orifice can be detected by a sensor from outside the patient's body.

17. The artificial sphincter recited in claim 12, wherein each of said stationary and rotatable rings has a respective split formed therein to permit said rings to be opened at said splits and positioned around the patient's lumen without requiring access to either end of the lumen or invading the lumen.

* * * * *